(12) United States Patent
Haadem

(10) Patent No.: US 7,422,756 B2
(45) Date of Patent: Sep. 9, 2008

(54) SKIN PREPARATION

(75) Inventor: Knut Haadem, Helsingborg (SE)

(73) Assignee: Knut Haadem AB, Helsingborg (SE)

( * ) Notice: Subject to any disclaimer, the term of this patent is extended or adjusted under 35 U.S.C. 154(b) by 758 days.

(21) Appl. No.: 10/478,915

(22) PCT Filed: Jun. 12, 2002

(86) PCT No.: PCT/SE02/01146

§ 371 (c)(1),
(2), (4) Date: Nov. 26, 2003

(87) PCT Pub. No.: WO02/100373

PCT Pub. Date: Dec. 19, 2002

(65) Prior Publication Data

US 2004/0166127 A1 Aug. 26, 2004

(30) Foreign Application Priority Data

Jun. 13, 2001 (SE) .................................... 0102087

(51) Int. Cl.
*A61K 8/02* (2006.01)
*A61K 31/56* (2006.01)
*A61K 47/12* (2006.01)

(52) U.S. Cl. ...................... 424/401; 514/169; 514/784; 514/947

(58) Field of Classification Search ................. 424/401; 514/169, 784, 947
See application file for complete search history.

(56) References Cited

U.S. PATENT DOCUMENTS 5,556,970 A * 9/1996 Kawasaki et al. ........... 554/190

FOREIGN PATENT DOCUMENTS

| EP | 0028457 | 5/1981 |
|---|---|---|
| EP | 0153203 | 8/1985 |
| EP | 0467218 | 1/1992 |
| EP | 0483689 | 5/1992 |
| EP | 0596135 | 5/1994 |
| EP | 1153595 | 11/2001 |
| FR | 2794366 | 12/2000 |
| WO | WO 90/01323 | 2/1990 |
| WO | WO 94/00127 | 1/1994 |
| WO | WO 98/30532 | 7/1998 |
| WO | WO 99/44582 | 9/1999 |
| WO | WO 99/53086 | 10/1999 |

* cited by examiner

*Primary Examiner*—Gina C Yu
(74) *Attorney, Agent, or Firm*—Buchanan Ingersoll & Rooney PC

(57) ABSTRACT

The invention concerns a skin preparation for moistening human skin comprising a combination of a component A and a component B, wherein A includes at least two saturated $C_9$-$C_{31}$ fatty acids selected from the group consisting of iso- and anteiso fatty acids, whereby component B consists of cholesterol in an amount of 5-15% by weight of component A.

17 Claims, No Drawings

SKIN PREPARATION

FIELD OF THE INVENTION

The present invention concerns a skin preparation. Specifically the invention concerns a preparation for human skin improvement.

BACKGROUND OF THE INVENTION

Skin preparations have been used for thousands of years to render a softer and more elastic sensation of the skin. These preparations are based on different components and work in different ways.

A frequently used component in skin preparations is lanolin, which is composed of hydrophobic esters, which oppose absorption of water. However, lanolin has been reported to cause allergic reactions in a high number of individuals.

Other frequently used components are water repellent films such as petrolatum, which however may cause maceration by preventing even normal moisture loss from the skin.

Furthermore, there are fats and oils of vegetable and animal origin, which are used in cosmetic formulations for their emollient, occlusive and moisturizing properties. Stability problems with these products require use of additives or stabilizers. These additives or stabilizers may however cause dermal problems.

Phospholipids have also been used as moisturizers in various creams and lotions. These lipids are complex fat substances found in living cells. Lecithin is an example of a typical phospholipid substance.

Still another type of skin preparations is disclosed in WO 9831399, which concerns preparations capable of forming an osmotic i.e. semi permeable membrane in the skin. These preparations are based on a combination of a lipophilic component, such as a fatty acid (stearic acid) or polysiloxane, and a hydrophilic component, such as triethanolamine.

Another type of skin preparations is based on vernix caseosa, which appears a cheesy deposit on the surface of human or animal foetuses and consists of about ⅓ of cholesterol esters. This type of preparations is described in e.g. U.S. Pat. No. 5,631,012 which concerns cosmetic compositions containing naturally occurring and/or synthesized vernix lipid mixtures in the same proportionate mixture. These compositions are described as moisturisers by functioning as a protective barrier between the skin and the environment.

Preparations based on vernix caseosa are also known from JP 10175843, which describes a skin composition containing vitamin E and cholesterol esters of mammal vernix origin. A disadvantage with cholesterol esters is that they do not penetrate the skin, but stays on its surface.

Another publication concerning compositions including vernix is disclosed in WO 99/44582. According to this publication a natural or synthetic vernix is dispersed in a film-forming amount in a biocompatible liquid such as dimethylsulfoxid, amniotic fluid and/or pulmonary surfactant to form a film. This publication also recognises the problem of achieving a controlled and uniform administration of the vernix substances through the skin.

From the above patent publications and other literature it is thus known that vernix could have a potential as a beneficial agent in skin preparations. A problem is however how to realize this effect and obtain a satisfactory effect.

OBJECTS OF THE INVENTION

It is an object of the present invention to provide a pharmaceutically active combination, which maintains the humidity and elasticity of human skin and is rapidly absorbed by the skin.

Another object is to provide cosmetic and/or medical preparations including this combination and conventionally used pharmaceutically and dermatologically acceptable carriers.

The formulations and methods by which the above objects may be accomplished are disclosed hereinafter.

SUMMARY OF THE INVENTION

The present invention is based on the discovery that, if components extractable from vernix and other substances having similar composition are combined with a specific amount of cholesterol, the problems with previously known skin preparations including such components/substances can be reduced or eliminated and skin preparations having a beneficial effect not previously observed on the skin are obtained. Specifically the present invention concerns a skin preparation for moistening human skin comprising a combination of a component A and a component B, wherein A includes at least two saturated $C_9$-$C_{31}$ fatty acids selected from the group consisting of iso- and anteiso fatty acids, and whereby component B consists of cholesterol in an amount of 5-15% by weight of component A. According to a preferred embodiment said iso-fatty acids constitute 30-70% by weight of component A and said anteiso-fatty acids constitute 70-30% by weight of component A.

DETAILED DESCRIPTION OF THE INVENTION

Specifically it has been found that component A, which is pharmacologically active, should be branched $C_9$-$C_{31}$ iso- and anteiso-fatty acids, preferably branched $C_{18}$-$C_{24}$ iso- and anteiso-fatty acids. These fatty acids have a low melting point giving high fluidity and are not easily oxidized. Due to the lower melting points of the anteiso- fatty acids it is presently believed that at least one of the at least two fatty acids should be an anteiso fatty acid. As an example component A could be made up by 12-methyltetradecanoic acid and isostearic acid and component B could be made up by 5-15, preferably 8-12% by weight, of component A.

However, indications have also been found that preparations wherein component A is made up by two (or more) iso fatty acids without any anteiso fatty acid(s) work satisfactorily. This is in accordance with my finding that the absorption into the skin of the branched iso and anteiso fatty acids is better compared with ordinary fatty acids, i.e. olive oil that has a slow absorption. Branched fatty acids are rare in nature, but are found in the form of cholesterol esters of the epidermis of the human skin where they also seem to have a key role in protecting the membrane and may have a positive effect on the microcirculation.

In order to obtain full effect of component A, it has been found that the addition of cholesterol (component B) is important.

Test results have shown that the barrier properties of the skin increase after treatment with the skin preparation according to the invention resulting in a decreased transepidermal water loss. Additional experimental studies have shown that the presence of cholesterol increases the miscibility and decreases the area ratio phases of the component A (measured by AFM, Atomic Force Microscopy), which in turn leads to a faster absorption when applied to the skin. The cholesterol content should be 5-15%, preferably 8-12%. The mechanism is probably that cholesterol minimizes the interfacial length between different phases.

Branched fatty acids useful in the skin preparations according to the present invention may be extracted from e.g. vernix caseosa, lanolin or butter, but may also be made synthetically or produced from straight chain fatty acids. A method of preparation of branched fatty acid is disclosed in WO 98/07680 and is hereby incorporated by reference. Another method for obtaining branched fatty acids which may be used according to the present invention is disclosed in WO/98/30552 which is also incorporated by reference.

The skin preparation may further comprise optional pharmaceutically and dermatologically acceptable excipients.

The physiologically active ingredient according to the invention is applied on the skin at a suitable concentration in a suitable dermatologically acceptable carrier. The concentration of the active ingredient naturally depends on the type of preparation and the type and amount of vehicle(s) and adjuvant(s) included in the carrier. Naturally, the active ingredient i.e. the branched fatty acids must be applied to the skin in a physiologically active amount.

The concentration of the branched fatty acids in a crème may be in the range 0.1-50% by weight, but is optimally in the range 10-30% by weight. An oil preparation may contain up to 90% by weight of the branched fatty acids.

The relative amount of the different branched fatty acids may be as in the cholesterol esters found in vernix caseosa or lanolin or may be a selection at least two of them.

A preliminary study has shown that the preparation according to the invention has an anti-inflammatory effect and may reduce/treat eczema.

EXAMPLES

Example 1

The following example is a description of the extraction of branched fatty acids from cholesterol esters in lanolin.

The lanolin used was Medilan liquid ultra™ from Croda Ltd Japan. 4 g of lanolin was accurately weighed into a 250 ml conical flask. 50 ml of ethanolic potassium hydroxide (0.5 mol/l) was added and a reflux condenser connected to the flask. The flask was heated and occasionally shaken until the fat was completely dissolved. The solution was boiled under reflux for 30 minutes. The solution was cooled and white crystals formed and precipitated. The supernatant of the solution was neutralized with HCl (1 mol/l) to pH 5.5 and then centrifuged. The supernatant was decanted from the pellet containing fatty acids and the remaining ethanol evaporated by rotation. The resulting concentration of the branched fatty acids was about 70%.

The fatty acid containing pellet was used for a skin preparation according to the present invention.

Table I shows the branched fatty acids from the fatty acid analysis of Medilan liquid Ultra™.

TABLE I

| Standard | Results (% of total fatty acids) | | | |
|---|---|---|---|---|
| | sample 1 | Sample 2 | Sample 3 | Sample 4 |
| C14:0 iso | 11.5 | 3.3 | 2.9 | 4.8 |
| C15:0 anteiso | 16.6 | 7.2 | 6.4 | 9.6 |
| C16:0 iso | 8.8 | 9.5 | 8.5 | 8.3 |
| C17:0 anteiso | 5.0 | 6.5 | 6.2 | 4.9 |
| C18:0 iso | 3.6 | 8.7 | 8.3 | 6.3 |

TABLE I-continued

| Standard | Results (% of total fatty acids) | | | |
|---|---|---|---|---|
| | sample 1 | Sample 2 | Sample 3 | Sample 4 |
| C19:0 anteiso | 6.1 | 14.3 | 13.9 | 12.9 |
| C20:0 iso | 2.7 | 11.5 | 11.7 | 8.6 |
| Total branched fatty acids (%) | 54.3 | 61.0 | 57.9 | 55.4 |

Example 2

Table II and III show examples of preparations according to the invention. The branched fatty acids were extracted from Medilan Liquid Ultra™ from Croda Ltd Japan and mixed with an ointment based on Ungventum™ from Merck Inc. The solution was obtained by heating the ingredients to 50° C. and thereafter mixing them.

TABLE II

Cream formula

| Ingredient | Amount (% by weight) |
|---|---|
| Concentrated branched fatty acids (from Medilan Liquid Ultra ™) | 25 |
| Cholesterol | 10 |
| Ungventum ™ | 40 |
| Distilled water | 25 |

TABLE III

Oil formula

| Ingredient | Amount % by weight |
|---|---|
| Concentrated branched fatty acids (from Medilan Liquid Ultra ™) | 90 |
| Cholesterol | 10 |

Example 3

The effect of the skin preparation on the barrier properties of the skin was examined with Trans Epidermal Water Loss (TEWL) provided by Servomed AB, Varberg. TEWL was measured at four different occasions with one minute intervals, where the mean value is reported. An oil with 90% by weight branched fatty acid and 10% by weight cholesterol was applied at the back of the left hand while the right hand served as control (untreated). The TEWL was measured before and three hours after the application of the-preparation (Table IV). The room temperature and the humidity were constant during the measurements.

TABLE IV

| TEWL ($g/m^2/h$) | | | |
|---|---|---|---|
| Creme formula according to the invention | | Control (no treatment) | |
| Before | After | Before | After |
| 15.8 | 13.6 | 17.3 | 18.0 |
| 11.9 | 6.1 | 12.7 | 9.4 |
| 8.0 | 6.8 | 7.0 | 6.8 |
| 11.3 | 9.2 | 13.0 | 12.7 |

The TEWL was significantly lower after the treatment with the active substance (p=0.03). In the control group there was no difference (p=n.s). As barrier function has been claimed to be improved with the use of Fenuril™ hand lotion, the most selling skin cream on the market at present and recommended by dermatologists, the product according to the invention was compared with Fenuril™. The results of the TEWL measurements for Fenuril™ and an untreated control is described in Table V.

TABLE V

| TEWL ($g/m^2/h$) | | | |
|---|---|---|---|
| Fenuril™ treatment control | | Control (no treatment) | |
| Before | After | Before | After |
| 14.8 | 15.9 | 16.6 | 16.6 |
| 14.2 | 10.3 | 14.6 | 9.5 |

There was no difference in TEWL after the Fenuril™ treatment and no difference in the control group (p=n.s).

Example 4

Five women used a skin preparation consisting of 90% branched fatty acids $C_{18}$-$C_{24}$ and 10% cholesterol for one week. All women had suffered from skin dryness for several years and had extensive experience with skin preparations. The branched fatty acids were produced from a special lanolin derivative (Medilan Liquid Ultra™). The skin preparation was applied at the back of the left hand and the right hand served as control. The results were judged with regard to skin elasticity, skin softness and speed of absorption. The results were divided up into very good, good, indifferent, bad and very bad. Four of the five women experienced the preparation as very good with regard to softness and elasticity. One experienced it as good. All women said that it was quickly absorbed. No side effects occurred. Three of the women experienced positive results of the finger pulpa they had used when applying the preparation.

Example 5

1) The same set-up as in example 3 was used. Isostearic acid was mixed with 12-methyltetradecanoic acid (anteiso C15) in equal parts. The ointment was divided in two parts, one without cholesterol and one mixed with 10% of cholesterol. One drop of the sample without cholesterol was applied at the right and one drop of the sample with cholesterol was applied at the left hand back. The skin surface for the application was 1 $cm^2$.

8 persons participated in the test, with mean age 48 years (62-37), 7 women and one man. The absorption time between application and absorption was measured and the result was statistically significant shorter for the ointment with cholesterol than for the one without as measured with Student T-test (p<0.01).

2) In this test the same compounds were used as in example 1, sample 2 containing branched fatty acids of 61.0%. The ointment was divided in two parts as in test 1) above, i.e. one sample with and one without 10% cholesterol. One drop of the two mixtures were tested on 1 $cm^2$ at the right and the left hand back as earlier. The same 8 persons as in test 1) participated in the test. Equivalent results were obtained as earlier, the ointment containing cholesterol was absorbed faster than the one without. The difference between the groups was statistically significant (p>0.01).

The conclusion of these tests is subsequently that the presence of cholesterol improve the absorption speed of the ointment on human skin.

3) 5 women underwent a test wherein isostearic acid and 12-methyltetradecanonic acid were mixed in equal parts and 10% cholesterol was then added. The ointment was applied at the back of the hand and TEWL (trans epidermal water loss) was measured before and three hours after application. The other hand served as control. TEWL was reduced with 18-34% after three hours compared with the controls were no difference occurred.

The invention claimed is:

1. A skin preparation for moistening human skin comprising a combination of a component A and a component B, wherein A is a mixture of one or more saturated $C_9$-$C_{31}$ iso fatty acid and one or more saturated $C_9$-$C_{31}$ anteiso fatty acid, and wherein component B consists of cholesterol in an amount of 5-15% by weight of component A.

2. The skin preparation according to claim 1 wherein the amount of cholesterol is 8-12% by weight of component A.

3. The skin preparation according to claim 1, wherein component A is made up by 30-70% by weight of iso-fatty acid(s) and 70-30% by weight of anteiso fatty acid(s).

4. The skin preparation according to claim 1, wherein the fatty acids of component A have 18-24 C atoms.

5. The skin preparation according to claim 1 wherein component A is made up by 12-methyltetradecanoic acid and isostearic acid and component B is 5-15% by weight of component A.

6. The skin preparation according to claim 1, wherein component A comprises two iso fatty acids.

7. The skin preparation according to claim 1, further comprising a pharmaceutically and dermatologically acceptable excipient.

8. The skin preparation according to claim 1, in the form of an ointment.

9. The skin preparation according to claim 1, wherein the fatty acids originate from vernix caseosa, lanolin or butter.

10. The skin preparation according to claim 2, wherein component A is made up by 30-70% by weight of iso-fatty acid(s) and 70-30% by weight of anteiso fatty acid(s).

11. The skin preparation according to claim 2, wherein the fatty acids of component A have 18-24 C atoms.

12. The skin preparation according to claim 3, wherein the fatty acids of component A have 18-24 C atoms.

13. The skin preparation according to claim 1, wherein component A is made up by 12-methyltetradecanoic acid and isostearic acid and component B is 8-12% by weight of component A.

14. The skin preparation according to claim 2, wherein component A comprises two iso fatty acids.

15. The skin preparation according to claim 2, further comprising a pharmaceutically and dermatologically acceptable excipient.

16. The skin preparation according to claim 2, in the form of an ointment.

17. The skin preparation according to claim 2, wherein the fatty acids originate from vernix caseosa, lanolin or butter.

* * * * *